United States Patent [19]
Hart

[11] Patent Number: 6,100,439
[45] Date of Patent: Aug. 8, 2000

[54] STYRENE CAUSTIC WASH EXTRACTION AID

[75] Inventor: Paul R. Hart, The Woodlands, Tex.

[73] Assignee: BetzDearborn Inc., Trevose, Pa.

[21] Appl. No.: 09/211,514

[22] Filed: Dec. 14, 1998

[51] Int. Cl.⁷ .................................. C07C 7/00; C07C 7/10
[52] U.S. Cl. .................. 585/808; 585/806; 585/837; 585/860; 585/861; 585/863
[58] Field of Search ...................... 585/806, 808, 585/837, 860, 861, 863

[56] References Cited

U.S. PATENT DOCUMENTS

| | | | |
|---|---|---|---|
| 3,017,426 | 1/1962 | Ruffing et al. | 206/465.9 |
| 3,247,242 | 4/1966 | McGarvey et al. | 260/486 |
| 3,632,626 | 1/1972 | Schneller et al. | 260/465.9 R |
| 5,154,831 | 10/1992 | Darian et al. . | |
| 5,250,174 | 10/1993 | Hart . | |
| 5,282,974 | 2/1994 | Hart . | |
| 5,476,988 | 12/1995 | Hart et al. | 585/860 |
| 5,481,059 | 1/1996 | Brock et al. . | |
| 5,675,055 | 10/1997 | Evans et al. | 585/858 |

*Primary Examiner*—Walter D. Griffin
*Assistant Examiner*—Tam M Nguyen
*Attorney, Agent, or Firm*—Steven D. Boyd

[57] ABSTRACT

Methods and compositions for improving the extraction of phenols from crude styrene using an aqueous caustic solution are disclosed. It has been discovered that aromatic or alkylammonium tailed multi-polyether headed surfactants and/or quaternary polyamines will improve this extraction, particularly in propylene oxide styrene monomer systems.

15 Claims, No Drawings

STYRENE CAUSTIC WASH EXTRACTION AID

FIELD OF THE INVENTION

The present invention provides for methods for improving the extraction of phenols in the propylene oxide styrene monomer process. More specifically, the present invention provides for methods for improving the removal of phenols from crude styrene with aqueous caustic.

BACKGROUND OF THE INVENTION

In the propylene oxide styrene monomer (POSM) process, methyl oxirane (propylene oxide) and ethenyl or vinyl benzene (styrene monomer) are co-produced. Molecular oxygen is reacted with ethylbenzene to form α-hydroperoxy ethylbenzene which is then subsequently reacted with propene to form propylene oxide and α-hydroxyethylbenzene, also known as methylbenzyl alcohol.

After removing the more volatile propylene oxide, the methylbenzyl alcohol is dehydrated to water and styrene monomer. These are co-distilled overhead and condensed into a water/oil separator, where the water forms a separate phase and is drained. The crude styrene phase is then extracted in a caustic wash drum with 5 to 10% of an aqueous caustic solution containing about 2 to 3% NaOH, sometimes with about an equal amount of a caustic solution recycled to remove phenolic byproducts of the above-described oxidation and epoxidation reactions.

The caustic extracted styrene is then rinsed in a water wash drum with 5 to 10% fresh water, also sometimes with about an equal amount recycled, to remove residual caustic and phenate salts from the crude styrene prior to distillation. Typically, the temperature of the extraction is about 100 to 110° F. The pH in the second stage is about 11.5 and in the first stage is about 14.

The present inventor has discovered a means to improve this extraction process while minimizing residual carryover of caustic and phenates to the styrene distillation towers. This method also helps eliminate the production and disposal as toxic waste of stable dispersion layers which otherwise accumulate in separation vessels.

DETAILED DESCRIPTION OF THE PREFERRED EMBODIMENTS

The present invention provides for an improved method for extracting phenols from crude styrene with aqueous caustic, the improvement comprising adding to the styrene an effective amount for the purpose of aiding extraction of an aromatic or alkylammonium tailed multi-polyether headed surfactant or a quaternary polyamine.

The aromatic or alkylammonium tailed multi-polyether headed surfactants (MPEHS) include those with hydrophobic "tails" comprising $C_3$ to $C_{18}$ alkylaryl diols to polyols and $C_3$ to $C_{22}$ alkyl or alkylaryl 1° or 2° amines. These are adducted with $C_2$ to $C_3$ alkylene oxides to form two or more hydrophilic heads per hydrophobe comprising separate polyether chains of degree of polymerization (dp) 3 to 30. The backbone and branches of the polymer contain only ether or amine linkages, and not, for example, esters or amides. Quaternary amines employ any convenient counterions, such as halides, sulfates, nitrates, phosphates, carboxylates, phenates, silicates, carbonates, or hydroxides.

Preferably, the multi-polyether headed surfactant comprises $C_4$ to $C_9$ alkylphenol-formaldehyde condensates of dp 4 to 8 adducted with ethylene oxide to form 4 to 8 polyether chains of dp 4 to 7 blended with the halide salt of linear $C_{12}$ to $C_{22}$ alkyl 2° amines adducted with ethylene oxide to form 2 polyether chains of dp 5 to 10.

The quaternary polyamines used in the present invention are those in which the backbone and branches of the polymer contain only ether or amine linkages and not, for example, esters or amides. The polyamine should have a degree of polymerization of about 60 to 6000 monomer units and an overall carbon to nitrogen or oxygen ratio of less than 10. These compounds are water soluble.

The quaternary polyamines include but are not limited to halides, sulfates, nitrates, phosphates, carboxylates, phenates, silicates, carbonates, or hydroxides of alkyl or alkylaryl quaternary amines. The preferred polyamines include but are not limited to poly(diallydimethylammonium chloride), or poly(DADMAC), having the formula:

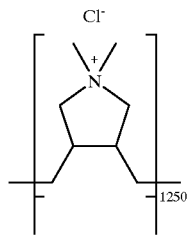

poly(N,N-dimethyl, 2-hydroxypropyleneammonium chloride), or poly(DMHPAC), having the formula:

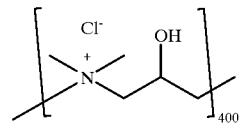

and poly(N,N-dimethyl, 3-(2-hydroxypropyleneamine) propylammonium chloride), or poly[DM(HPA)PAC], having the formula:

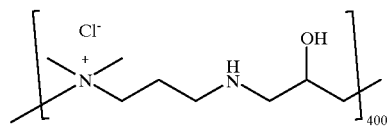

The poly(DMHPAC) compound may be formed by reacting about equimolar amounts of 3-chloromethyl-1,2-oxirane (epichlorohydrin of EPI) with dimethylamine (DMA).

The poly[DM(HPA)PAC] may be formed by reacting about equimolar amounts of EPI and dimethylaminopropylamine (DMAPA).

The present inventor has discovered that these extraction aids assist in fluidizing, solubilizing and removing the surfactant barrier to improve extraction efficiency. This minimizes the caustic carryover to the crude styrene distillation section and eliminates the production and disposal of the dispersion layer.

The multi-polyether headed surfactants are preferably fed as solutions in aqueous or organic solvents that are compatible with both the MPEH's and the POSM process. The organic solvents include high boiling (i.e. greater than 400° F.) aromatic hydrocarbons, glycol ethers, such as 2-n-butoxy-2-ethoxyethanol (butyl carbitol), and native aromatic alcohols such as α-hydroxyethylbenzene, which is most preferred.

Preferably the solutions are fed to the influent, unwashed styrene. The solutions may also be fed to the interstage, washed but not rinsed styrene. Preferably from about 3 to about 30 parts of MPEH per million parts of styrene are fed.

The quaternary polyamines are preferably fed an aqueous solution to the influent caustic wash water or the fresh rinse water or most preferably both the caustic wash and rinse water, prior to mixing with the styrene.

The quaternary polyamines are fed in amounts ranging from about 1 part to about 100 parts polyamine per million parts of water with a range of about 3 to about 30 preferred, or about 0.1 part to about 10 parts per million parts of styrene with a range of about 0.2 to about 2.0 parts preferred.

The following examples are intended to show the efficacy of the present invention and should not be construes as limiting the scope of the invention.

EXAMPLES

In order to find a counteractant to the barrier soaps, which tend to accumulate at the interface of the extraction vessels, a sample of concentrated soap in an 18% oil-in-water emulsion from the second stage of a Southwestern U.S. POSM caustic wash unit was taken.

Selected candidates were screened using the following procedure:

1. Add 100 mL of sample to 6 oz. Rx bottle
2. Heat the bottle to 105° F. in a 105° F. water bath
3. Treat the sample with chemical at 105° F.
4. Shake the bottle with a 3 inch stroke at 60 cps for 1 minute on a mechanical shaker
5. Place the bottle back into a 105° F. bath
6. Record rate and degree to which soapy appearance disappears.

Table A lists the chemicals that were tested.

TABLE A

A Branched nonylphenol-formaldehyde condensate of dp 4–8 adducted with propyl- and ethylene oxides to form 4–8 polyether chains of dp 7–10 each B 2,2-bis-p-phenoxyhydroxypropyletherpoly (propylether) propane of dp 0–2 adducted with ethylene oxide to form 4–8 polyether chains of dp 4–8 each C Poly(N,N-dimethyl, 2-hydroxypropyleneammonium and 3-(2-hydroxypropyleneamine) propylammonium, chlorides)

D Poly(diallydimethyl ammonium chloride)

The results of this screening are shown in Tables I & II. The "top oil" described as "opaque white" was found to be a water continuous phase. "Translucent" (or "transluc.") and "transparent" (or "transpar.") indicate an oil continuous phase, with and without significant entrained water, respectively. "Transparent" indicates text is readable through the phase, though some dispersed material remains. "Clear" indicates phase is substantially free of any dispersed material. Within a given opacity classification, the color indicates the relative amount of foreign material present in the phase, with brown>tan>amber>yellow>white.

TABLE I

| Treatment | | 5 Minutes | | | 30 Minutes | | | 60 Minutes | | |
| --- | --- | --- | --- | --- | --- | --- | --- | --- | --- | --- |
| Chemical | ppm Act | Top Oil | Bottom Water | I/F | Top Oil | Bottom Water | I/F | Top Oil | Bottom Water | I/F |
| blank | 0 | opaque white | opaque white | much soap | opaque white | opaque white | much soap | opaque white | opaque white | much soap |
| A | 3 | opaque white | opaque white | much soap | opaque white | opaque white | much soap | opaque white | opaque white | much soap |
| A | 7.5 | opaque white | opaque white | much soap | opaque white | opaque white | much soap | opaque white | opaque white | much soap |
| A | 15 | opaque white | opaque white | much soap | opaque white | opaque white | much soap | opaque white | opaque white | much soap |
| A | 30 | opaque white | opaque white | much soap | opaque white | opaque white | much soap | opaque white | opaque white | much soap |
| A | 60 | opaque white | opaque white | much soap | opaque white | opaque white | much soap | opaque white | opaque white | much soap |
| A | 120 | opaque white | opaque white | much soap | opaque white | opaque white | much soap | opaque white | opaque white | much soap |
| A | 240 | opaque white | opaque white | much soap | opaque white | opaque white | much soap | opaque white | opaque white | much soap |
| C | 1.5 | 50% transluc. brown | translucent | much soap | 75% transluc. brown | translucent | much soap | 80% transparent | opaque white | much soap |
| C | 3.75 | 80% transluc. brown | translucent | little soap | 90% transluc. brown | transparent | little soap | 90% transpar. amber | translucent | much soap |
| C | 7.5 | all transluc. brown | transparent | no soap | 100% transpar. | transparent | no soap | 100% transpar. | transparent | no soap |
| C | 15 | 25% transparent, | transparent | much soap | 50% transparent | transparent | much soap | 80% transparent | transparent | much soap |
| C | 30 | opaque white | translucent | much soap | opaque white | translucent | much soap | 25% transparent | translucent | much soap |

TABLE I-continued

| Treatment | | Post-Treatment Appearance Readings | | | | | | | | |
|---|---|---|---|---|---|---|---|---|---|---|
| | | 5 Minutes | | | 30 Minutes | | | 60 Minutes | | |
| Chemical | ppm Act | Top Oil | Bottom Water | I/F | Top Oil | Bottom Water | I/F | Top Oil | Bottom Water | I/F |
| C | 60 | opaque white | opaque white | much soap | opaque white | opaque white | much soap | 10% trans-parent | opaque white | much soap |
| C | 120 | opaque white | opaque white | much soap | opaque white | opaque white | much soap | 10% trans-parent | opaque white | much soap |
| D | 1.5 | opaque white | opaque white | much soap | opaque white | opaque white | much soap | 10% trans-parent | opaque white | much soap |
| | 3.75 | opaque white | opaque white | much soap | 25% trans-luc. brown | opaque white | much soap | 25% trans-parent | opaque white | much soap |
| D | 7.5 | 50% trans-luc. brown | opaque white | much soap | 50% trans-luc. brown | opaque white | much soap | 50% trans-par. amber | opaque white | much soap |
| D | 15 | 90% trans-luc. brown | trans-parent | little soap | 90% trans-iuc. brown | clear | little soap | 90% trans-parent | clear | little soap |
| D | 30 | 25% trans-luc. brown | trans-parent | much soap | 50% trans-luc. brown | trans-parent | much soap | 50% trans-parent | trans-parent | much soap |
| D | 60 | opaque white | trans-lucent | much soap | opaque white | trans-lucent | much soap | much soap | opaque white | much soap |
| D | 120 | opaque white | trans-lucent | much soap | opaque white | trans-lucent | much soap | much soap | opaque white | much soap |

TABLE II

| Treatment | | Post Treatment Appearance Readings | | | | | | | | | | | |
|---|---|---|---|---|---|---|---|---|---|---|---|---|---|
| | | 5 Minutes | | | 15 Minutes | | | 30 Minutes | | | 60 Minutes | | |
| Chemical | ppm Act | Top Oil | Bottom Water | I/F | Top Oil | Bottom Water | I/F | Top Oil | Bottom Water | I/F | Top Oil | Bottom Water | I/F |
| blank | 0 | opaque white | opaque white | much soap | opaque white | opaque white | little soap | opaque white | opaque white | little soap | opaque white | opaque white | little soap |
| B | 2.3 | opaque white | opaque white | much soap | opaque white | opaque white | little soap | opaque white | trans-lucent | little soap | opaque white | opaque white | little soap |
| B | 4.6 | opaque white | opaque white | much soap | opaque white | opaque white | little soap | opaque white | trans-lucent | little soap | opaque white | opaque white | little soap |
| B | 9.2 | opaque white | opaque white | much soap | opaque white | opaque white | little soap | opaque white | trans-lucent | little soap | opaque white | opaque white | little soap |
| B | 18.4 | opaque white | opaque white | much soap | opaque white | opaque white | little soap | opaque white | trans-lucent | little soap | opaque white | opaque white | little soap |
| B | 36.5 | opaque white | opaque white | much soap | opaque white | opaque white | tittte soap | opaque white | trans-lucent | little soap | opaque white | opaque white | little soap |
| B | 73.6 | opaque white | opaque white | much soap | opaque white | opaque white | little soap | opaque white | trans-lucent | little soap | opaque white | opaque white | little soap |

Tables I and II show that D from 1.5 to 30 ppm active and, even more so C, from 1.5 to 60 ppm active, per emulsion, were able to remove the barrier surfactants and allow the dispersed crude styrene to coalesce into a recoverable, phenate and caustic depleted, clear organic phase on top, an emulsion free interface between the oil and water layers and a clearer, less wasteful and hazardous water layer. The MPEH's, which have broken other types of emulsions not containing synthetic stabilizers in other applications at near neutral pH (5–9), had no significant effect on accumulated surfactants such as these at alkaline pH (11–14).

These results imply that the phenol extraction process would be improved by feeding about 9 ppm of C per water (0–6 ppm active per oil at 6.6% water wash) into the water to the vessel accumulating soapy emulsion. The sample above was taken from stage 2 but if the treatment were applied either additionally or instead to stage 1 to keep soap from carrying over, better extraction may result.

A second test was run to test an agent's ability to promote formation of an emulsion with which to extract the phenol but which would also not impede the reaction of the phenols with the caustic, the transfer of the phenate to the water droplets, or the subsequent coalescence and removal of the droplets from the styrene. Samples of the first stage crude styrene effluent and the first stage caustic brine effluent (containing 0.8% sodium hydroxide and 0.5% sodium phenates) were taken and used to recreate the first stage extraction step in the laboratory. A variety of candidate extraction aids were screened using the following procedure:

1. Pour 86 mL crude styrene and 14 mL caustic water into Rx bottle
2. Heat to 105° F. in a water bath
3. Treat with chemical at 105° F. in duplicate
4. Shake the bottle with a 3 inch stroke at 240 cps for 1 minute on a mechanical shaker
5. Place the bottle into 105° F. bath
6. Record degree to which an initial milky appearance forms
7. Record the rate and degree the milky appearance disappears for 60 minutes.

Table B presents the additional chemicals tested.

TABLE B

E Linear dodecylbenzene sulfonic acid, nonylphenol-formaldehyde condensates of dp 4–8 adducted with ethylene oxide to form 4–8 polyether chains of dp 4–7, and a nonylphenol ethoxylate F Branched nonylphenol-formaldehyde condensate of dp 4–8 adducted with ethylene oxide to form 4–8 polyether chains of dp 4–7 and poly(propylether diol) adducted with ethylene oxide to form 2 polyether chains of dp 12–24

G Branched nonylphenol-formaldehyde condensates of dp 4–8 adducted with ethylene oxide to form 4–8 polyether chains of dp 4–7

H Branched nonylphenol-formaldehyde condensates of dp 4–8 adducted with ethylene oxide to form 4–8 polyether chains of dp 4–7 and halide salts of linear $C_{12}$ to $C_{22}$ alkyl 2° amines adducted with ethylene oxide to form 2 polyether chains of dp 5–10

I Poly(propylether diol) adducted with ethylene oxide to form 2 polyether chains of dp 12–24

J Halide and carboxylate slats of linear $C_{12}$ to $C_{22}$ alkyl 1° and 2° amines adducted with ethylene oxide to form 2–3 polyether chains of dp 1–10

The results of this testing are presented in Tables III to VII.

TABLE III

| | | Post Treatment Appearance Readings | | | | | | | | | | | |
|---|---|---|---|---|---|---|---|---|---|---|---|---|---|
| Treatment | | 5 Minutes | | | 15 Minutes | | | 30 Minutes | | | 60 Minutes | | |
| Chemical | ppm Act | Top Oil | Bottom Water | I/F | Top Oil | Bottom Water | I/F | Top Oil | Bottom Water | I/F | Top Oil | Bottom Water | I/F |
| blank | 0 | translucent, amber | translucent, brown | little soap | translucent, amber | translucent, amber | little soap | transparent, amber | translucent, amber | little soap | transparent, amber | transparent, amber | little soap |
| B | 5.8 | transparent, amber | translucent, amber | little soap | transparent, yellow | transparent, yellow | little soap | transparent, yellow | transparent, yellow | little soap | clear, yellow | transparent, yellow | little soap |
| B | 12 | transparent, amber | translucent, amber | little soap | transparent, yellow | clear, yellow | little soap | transparent, yellow | transparent, yellow | little soap | clear, yellow | transparent, yellow | little soap |
| B | 23 | translucent, amber | translucent, amber | little soap | transparent, amber | clear, yellow | little soap | transparent, amber | transparent, yellow | little soap | transparent, yellow | transparent, yellow | little soap |
| B | 46 | translucent, amber | translucent, amber | little soap | translucent, amber | clear, yellow | little soap | translucent, amber | transparent, yellow | little soap | translucent, amber | transparent, yellow | little soap |
| B | 92 | translucent, brown | translucent, amber | little soap | translucent, brown | clear, yellow | little soap | translucent, brown | transparent, yellow | little soap | translucent, amber | transparent, yellow | little soap |
| B | 184 | opaque brown | translucent, amber | little soap | opaque brown | clear, yellow | little soap | translucent, brown | transparent, yellow | little soap | translucent, brown | transparent, yellow | little soap |
| D | 7.5 | translucent, amber | opaque brown | little soap | translucent, amber | translucent, amber | little soap | translucent, amber | translucent, amber | little soap | transparent, amber | transparent, yellow | little soap |
| D | 15 | translucent, amber | opaque brown | little soap | translucent, amber | clear, yellow | little soap | translucent, amber | translucent, amber | little soap | translucent, amber | transparent, yellow | little soap |
| D | 30 | translucent, tan | opaque brown | much soap | translucent, tan | clear, yellow | little soap | translucent, tan | translucent, amber | little soap | translucent, amber | transparent, yellow | little soap |
| D | 60 | translucent, brown | opaque brown | much soap | translucent brown | clear yellow | much soap | translucent, tan | translucent, amber | much soap | translucent brown | transparent, yellow | little soap |
| D | 120 | translucent, brown | opaque brown | much soap | trans lucent brown | clear yellow | much soap | translucent, brown | translucent, amber | much soap | translucent brown | transparent, yellow | much soap |
| D | 240 | opaque brown | opaque brown | much soap | trans lucent brown | clear yellow | much soap | translucent, brown | translucent, amber | much soap | translucent brown | transparent, yellow | much soap |

TABLE IV

| Treatment | | 5 Minutes | | | 30 Minutes | | | 60 Minutes | | |
|---|---|---|---|---|---|---|---|---|---|---|
| Chemical | ppm Act | Top Oil | Bottom Water | I/F | Top Oil | Bottom Water | I/F | Top Oil | Bottom Water | I/F |
| blank | 0 | translucent, brown | translucent, brown | little soap | translucent, amber | translucent, amber | little soap | transparent, amber | transparent, amber | little soap |
| B | 1.1 | translucent, amber | transparent, amber | little soap | transparent, amber | transparent, yellow | little soap | transparent, yellow | transparent, yellow | little soap |
| B | 2.3 | transparent, amber | transparent, amber | little soap | transparent, yellow | transparent, yellow | little soap | clear, yellow | transparent, yellow | little soap |
| B | 5.8 | transparent, amber | transparent, amber | little soap | transparent, yellow | transparent, yellow | little soap | clear, yellow | transparent, yellow | little soap |
| B/D | 5.8/0.15 | transparent, amber | transparent, yellow | little soap | transparent, yellow | transparent, yellow | little soap | transparent, yellow | transparent, yellow | little soap |
| B/D | 5.8/0.3 | translucent, amber | transparent, yellow | little soap | transparent, yellow | transparent, yellow | little soap | transparent, yellow | transparent, yellow | little soap |
| B/D | 5.8/0.6 | translucent, amber | transparent, yellow | little soap | transparent, amber | transparent, yellow | little soap | transparent, yellow | transparent, yellow | little soap |
| B/D | 2.3/0.15 | translucent, amber | transparent, yellow | little soap | transparent, amber | transparent, yellow | little soap | transparent, yellow | transparent, yellow | little soap |
| B/D | 2.3/0.3 | translucent, amber | transparent, yellow | little soap | trans parent amber | transparent, yellow | little soap | transparent, yellow | transparent, yellow | little soap |
| B/D | 2.3/0.6 | translucent, amber | transparent, yellow | little soap | trans parent amber | transparent, yellow | little soap | transparent, yellow | transparent, yellow | little soap |
| D | 3.8 | translucent, brown | translucent, amber | little soap | translucent, amber | transparent, amber | little soap | transparent, amber | transparent, yellow | little soap |

TABLE V

| Treatment | | 5 Minutes | | | 30 Minutes | | | 60 Minutes | | |
|---|---|---|---|---|---|---|---|---|---|---|
| Chemical | ppm Act | Top Oil | Bottom Water | I/F | Top Oil | Bottom Water | I/F | Top Oil | Bottom Water | I/F |
| blank | 0 | translucent, amber | translucent, brown | little soap | translucent, amber | translucent, amber | little soap | transparent, amber | transparent, amber | little soap |
| E | 8.2 | transparent, amber | translucent, amber | little soap | transparent, yellow | transparent, yellow | little soap | transparent, yellow | transparent, yellow | little soap |
| F | 6.2 | transparent, amber | translucent, amber | little soap | transparent, yellow | transparent, yellow | little soap | transparent, yellow | transparent, | little soap |
| G | 6 | transparent, amber | translucent, amber | little soap | almost clear, yellow | transparent, yellow | little soap | clear, yellow | transparent, yellow | little soap |
| A | 6 | transparent, amber | translucent, amber | little soap | clear, yellow | transparent, yellow | little soap | clearer, yellow | transparent, yellow | little soap |
| H | 4 | transparent, amber | translucent, amber | little soap | clearer, yellow | transparent, yellow | little soap | clearest, yellow | transparent, yellow | least soap |
| J | 3 | transparent, amber | translucent, amber | little soap | transparent, yellow | transparent, yellow | little soap | almost clear, yellow | transparent, yellow | little soap |

TABLE V-continued

Post Treatment Appearance Readings

| Treatment | | 5 Minutes | | | 30 Minutes | | | 60 Minutes | | |
|---|---|---|---|---|---|---|---|---|---|---|
| Chemical | ppm Act | Top Oil | Bottom Water | I/F | Top Oil | Bottom Water | I/F | Top Oil | Bottom Water | I/F |
| B | 4.6 | translucent, amber | translucent, amber | little soap | transparent, yellow | transparent, yellow | little soap | almost clear, yellow | transparent, yellow | little soap |
| I | 7.2 | translucent, brown | translucent, amber | little soap | translucent, amber | translucent, amber | little soap | translucent, amber | transparent, yellow | little soap |

TABLE VI

Post Treatment Appearance Readings

| Treatment | | 5 Minutes | | | 30 Minutes | | | 60 Minutes | | |
|---|---|---|---|---|---|---|---|---|---|---|
| Chemical | ppm Act | Top Oil | Bottom Water | I/F | Top Oil | Bottom Water | I/F | Top Oil | Bottom Water | I/F |
| C | 0.3 | translucent, amber | opaque, brown | little soap | translucent, amber | translucent, amber | little soap | transparent, amber | transparent, yellow | little soap |
| C | 0.6 | translucent, amber | translucent, amber | little soap | transparent, amber | translucent, amber | little soap | transparent, amber | transparent, yellow | little soap |
| C | 1.2 | translucent, amber | translucent, amber | little soap | transparent, amber | translucent, amber | little soap | transparent, amber | transparent, yellow | little soap |
| C | 2.4 | translucent, amber | translucent, amber | little soap | transparent, amber | translucent, amber | little soap | transparent, amber | transparent, yellow | little soap |
| C | 4.8 | translucent, amber | opaque, brown | little soap | transparent, amber | translucent, amber | little soap | transparent, amber | transparent, yellow | little soap |
| C | 9.6 | translucent, brown | opaque, brown | little soap | translucent, amber | translucent, amber | little soap | transparent, amber | transparent, yellow | little soap |
| B | 2.3 | transparent, amber | translucent, amber | little soap | transparent, yellow | transparent, yellow | little soap | almost clear, yellow | transparent, yellow | little soap |
| B | 4.6 | transparent, amber | translucent, amber | little soap | almost clear, yellow | transparent, yellow | little soap | almost clear, yellow | transparent, yellow | little soap |
| H | 2.0 | transparent, amber | translucent, amber | little soap | clear, yellow | transparent, yellow | little soap | clear, yellow | transparent, yellow | no soap |
| H | 4.0 | transparent, amber | translucent, amber | little soap, | clear, yellow | transparent, yellow | little soap | clear, yellow | transparent, yellow | no soap |

TABLE VII

Post Treatment Appearance Readings

| Treatment | | 5 Minutes | | | 30 Minutes | | | 60 Minutes | | |
|---|---|---|---|---|---|---|---|---|---|---|
| Chemical | ppm Act | Top Oil | Bottom Water | I/F | Top Oil | Bottom Water | I/F | Top Oil | Bottom Water | I/F |
| blank | 0 | translucent, amber | translucent, brown | little soap | transparent, amber | translucent, amber | little soap | transparent, amber | transparent, amber | little soap |

TABLE VII-continued

| Treatment | | 5 Minutes | | | 30 Minutes | | | 60 Minutes | | |
|---|---|---|---|---|---|---|---|---|---|---|
| Chemical | ppm Act | Top Oil | Bottom Water | I/F | Top Oil | Bottom Water | I/F | Top Oil | Bottom Water | I/F |
| A | 6 | transparent, amber | translucent, amber | little soap | clear, yellow | transparent, yellow | little soap | clearer, yellow | transparent, yellow | no soap |
| A/C | 6/0.3 | transparent, amber | translucent, amber | little soap | clear, yellow | transparent, yellow | little soap | clearer, yellow | transparent, yellow | no soap |
| A/C | 6/0.6 | transparent, amber | translucent, amber | little soap | transparent, yellow | transparent, yellow | little soap | clear, yettow | transparent, yellow | no soap |
| A/C | 6/0.9 | transparent, amber | translucent, amber | little soap | transparent, amber | transparent, yellow | little soap | transparent, yellow | transparent, yellow | no soap |
| H | 4 | transparent, amber | translucent, amber | little soap | clear, yellow | transparent, yellow | little soap | clearest, yellow | transparent, yellow | no soap |
| H/C | 4/0.3 | transparent, amber | translucent, amber | little soap | clear, yellow | transparent, yellow | little soap | clearest, yellow | transparent, yellow | no soap |
| H/C | 4/0.6 | transparent, amber | translucent, amber | little soap | transparent, yellow | transparent, yellow | little soap | transparent, yelllow | transparent, yellow | no soap |
| H/C | 4/0.9 | transparent, amber | translucent, amber | little soap | transparent, yellow | transparent, yellow | little soap | transparent, yellow | transparent, yellow | no soap |
| B | 4.6 | transparent, amber | translucent, amber | little soap | transparent, yellow | transparent, yellow | little soap | atmost clear, yellow | transparent, yellow | no soap |
| B/C | 4.6/0.3 | transparent, amber | translucent, amber | little soap | transparent, yellow | transparent, yellow | little soap | transparent, yellow | transparent, yellow | little soap |
| B/C | 4.6/0.6 | transparent, amber | translucent, amber | little soap | transparent, yelloow | transparent, yellow | little soap | transparent, yellow | transparent, yellow | little soap |
| B/C | 4.6/0.9 | translucent, amber | translucent, brown | little soap | transparent, amber | transparent, yellow | little soap | transparent, amber | transparent, yellow | little soap |

The data in Tables II and IV show that the aromatic tailed MPEH's achieved the best results for forming a fluid, extractive emulsion of caustic-in-styrene.

The data in Table V demonstrate that aromatic and alkylammonium tailed MPEH's were effective while blends of aromatic and alkylammonium tailed MPEH's were even more effective.

The data in Table VI also show the aromatic and alkylammonium tailed MPEH blend to be best based on caustic removal. Table VII demonstrates that small amounts of a quaternary polyamine can be added in conjunction with the aromatic and/or alkylammonium tailed MPEH's without harm to the extraction process.

Clarified top oil from the previous test and additional DI water were used to simulated the second stage rinse. Additional treatments and controls with no further treatment were tested using the following procedure:

1. Thief 70 mL clarified top oil from previous test and place in another Rx bottle.
2. Add 5.25 mL (7%) DI water to 2nd bottle.
3. Heat to 105° F. in water bath.
4. To one of each duplicate, add an additional 1 ppm (product) C.
5. Shake the bottles with a 3 inch stroke at 240 cps for 1 minute on a mechanical shaker.
6. Place the bottles back into 105° F. bath.
7. Record degree to which an initial milky appearance forms.
8. Record the rate and degree the milky appearance disappears for 60 minutes.

The results of this testing are presented in Table VIII.

TABLE VIII

| Treatment | | | 5 Minutes | | | 30 Minutes | | | 60 Minutes | | |
|---|---|---|---|---|---|---|---|---|---|---|---|
| Chemical | ppm orig | ppm add | Top Oil | Bottom Water | I/F | Top Oil | Bottom Water | I/F | Top Oil | Bottom Water | I/F |
| blank | 0 | 0 | trans- | clear, | very | trans- | clear, | much | trans- | clear | much |

TABLE VIII-continued

| Treatment | | | Post Treatment Appearance Readings | | | | | | | | |
|---|---|---|---|---|---|---|---|---|---|---|---|
| | | | 5 Minutes | | | 30 Minutes | | | 60 Minutes | | |
| Chemical | ppm orig | ppm add | Top Oil | Bottom Water | I/F | Top Oil | Bottom Water | I/F | Top Oil | Bottom Water | I/F |
| | | | lucent, brown | yellow | much soap | lucent, amber | white | soap | parent, amber | white | soap |
| A | 6 | 0/0 | translucent, brown | translucent, amber | much soap | clear, white | clear, white | much soap | clear, white | clear, white | little soap |
| A/C | 6/0.3 | 0/0 | translucent, brown | translucent, brown | much soap | translucent, brown | clear, white | much soap | transparent, amber | clear, white | much soap |
| A/C | 6/0.6 | 0/0 | translucent, brown | translucent, brown | much soap | translucent, brown | clear, white | much soap | translucent, brown | clear, white | much soap |
| A/C | 6/0.9 | 0/0 | translucent, brown | translucent, brown | much soap | translucent, brown | clear, white | much soap | translucent, brown | clear, white | much soap |
| H | 4 | 0/0 | transparent, yellow | clear, white | little soap | clear, white | clear, white | no soap | clearer, white | clear, white | no soap |
| H/C | 4/0.3 | 0/0 | transparent, yellow | clear, white | little soap | clear, white | clear, white | no soap | clearer, white | clear, white | no soap |
| H/C | 4/0.6 | 0/0 | transparent, yellow | clear, white | little soap | clear, white | clear, white | no soap | clearer, white | clear, white | no soap |
| H/C | 4/0.9 | 0/0 | transparent, yellow | clear, white | little soap | clear, white | clear, white | no soap | clearer, white | clear, white | no soap |
| B | 4.6 | 0/0 | translucent, brown | clear, white | no soap | transparent, yellow | clear, white | much soap | clear, yellow | clear, white | little soap |
| B/C | 4.6/0.3 | 0/0 | translucent, brown | clear, white | no soap | translucent, brown | clear, white | much soap | translucent, amber | clear, white | little soap |
| B/C | 4.6/0.6 | 0/0 | translucent, brown | clear, white | no soap | translucent, brown | clear, white | much soap | translucent, amber | clear, white | much soap |
| B/C | 4.6/0.9 | 0/0 | translucent, brown | clear, white | no soap | translucent, brown | clear, white | much soap | translucent, amber | clear, white | much soap |
| A/C | 6/0 | 0/0.3 | translucent, brown | translucent, brown | much soap | translucent, brown | clear, white | much soap | clear, yellow | clear, white | much soap |
| A/C | 6/0.3 | 0/0.3 | translucent, brown | translucent, brown | much soap | translucent, brown | clear, white | much soap | translucent, amber | clear, white | much soap |
| A/C | 6/0.6 | 0/0.3 | translucent, brown | translucent, brown | much soap | translucent, brown | clear, white | much soap | translucent, amber | clear, white | much soap |
| A/C | 6/0.9 | 0/0.3 | translucent, brown | translucent, brown | much soap | translucent, brown | clear, white | much soap | translucent, amber | clear, white | much soap |
| H/C | 4/0 | 0/0.3 | translucent, amber | clear, white | no soap | clear, white | clear, white | no soap | clearest, white | clear, white | stays clean on agit'n |
| H/C | 4/0.3 | 0/0.3 | translucent, amber | clear, white | no soap | clear, white | clear, white | no soap | clearest, white | clear, white | stays cleanest on agit'n* |
| H/C | 4/0.6 | 0/0.3 | translucent, amber | clear, white | no soap | clear, white | clear, white | no soap | clearest, white | clear, white | stays clean on agit'n |
| H/C | 4/0.9 | 0/0.3 | translucent, amber | clear, white | no soap | clear, white | clear, white | no soap | clearest, white | clear, white | stays clean on agit'n |
| B/C | 4.6/0 | 0/0.3 | translucent, brown | transparent, vesicles | much soap | translucent, brown | clear, white | much soap | clear, yellow | clear, white | much soap |
| B/C | 4.6/0.3 | 0/0.3 | translucent, brown | transparent, vesicles | much soap | translucent, brown | clear, white | much soap | transparent, amber | clear, white | much soap* |
| B/C | 4.6/0.6 | 0/0.3 | translucent, brown | transparent, vesicles | much soap | translucent, brown | clear, white | much soap | transparent, amber | clear, white | much soap |

TABLE VIII-continued

| Treatment | | | Post Treatment Appearance Readings | | | | | | | | |
|---|---|---|---|---|---|---|---|---|---|---|---|
| | | | 5 Minutes | | | 30 Minutes | | | 60 Minutes | | |
| Chemical | ppm orig | ppm add | Top Oil | Bottom Water | I/F | Top Oil | Bottom Water | I/F | Top Oil | Bottom Water | I/F |
| B/C | 4.6/0.9 | 0/0.3 | translucent, brown | transparent, vesicles | much soap | translucent, brown | clear, white | much soap | transparent, amber | clear, white | much soap |

*Cleans up and doesn't redisperse after sitting overnight.

These data demonstrate that treatment H at 4 ppm active or at 4 ppm active combined in Stage 1 with Treatment C at 0.3 to 1.0 ppm active would produce improved extraction (crystal clear top oil), less waste (crystal clear on bottom) and better process control and consistency (emulsion free interface in 30 minutes). The addition of an additional 0.3 ppm active Treatment C in Stage 2 provides this all at an increased throughput capacity.

To find a more robust treatment capable of recovering from intermittent excursions or cumulative retention of soap production and/or entrainment, such as the initial state to the system studied, a realistic amount of the accumulated emulsion withdrawn from the interface of the 2nd stage, used in the initial testes (Table I and II), was added into each of the test bottles from the previous test and reshaken using the following procedure:

1. Add 2 mL 2nd stage interface emulsion to each bottle from previous test
2. (Do not add more chemical treatment.)
3. Maintain at 105° F. in water bath.
4. Shake the bottles with a 3 inch stroke at 240 cps for 1 minute on a mechanical shaker.
5. Place the bottles back into 105° F. bath.
6. Record degree to which an initial milky appearance forms.
7. Record the rate and degree the milky appearance disappears for 60 minutes.

The results are shown in Table IX, where the treatment histories are those of Table VIII.

TABLE IX

| Treatment | | Post Treatment Appearance Readings | | | | | |
|---|---|---|---|---|---|---|---|
| | | 30 Minutes | | | 60 Minutes | | |
| Chemical | ppm total | Top Oil | Bottom Water | I/F | Top Oil | Bottom Water | I/F |
| blank | 0 | translucent, amber | translucent, brown | much soap | clear, white | translucent, brown | much soap |
| A | 6 | transparent, yellow | translucent, amber | much soap | clear, white | translucent, brown | much soap |
| A/C | 6/0.3 | transparent, amber | translucent, brown | much soap | clear, yellow | translucent, brown | much soap |
| A/C | 6/0.6 | translucent, amber | translucent, brown | much soap | transparent, yellow | translucent, brown | much soap |
| A/C | 6/0.9 | translucent, brown | translucent, brown | much soap | translucent, amber | translucent, brown | much soap |
| H | 4 | clear, yellow | translucent, brown | little soap | clear, white | translucent, amber | little soap |
| H/C | 4/0.3 | transparent, yellow | translucent, brown | little soap | clear, white | translucent, amber | little soap |
| H/C | 4/0.6 | transparent, yellow | translucent, brown | little soap | clear, white | translucent, amber | little soap |
| H/C | 4/0.9 | transparent, amber | translucent, brown | little soap | clear, white | translucent, amber | little soap |
| B | 4.6 | transparent, yellow | translucent, brown | much soap | clear, white | translucent, brown | much soap |
| B/C | 4.6/0.3 | transparent, amber | translucent, brown | much soap | transparent, yellow | translucent, brown | much soap |
| B/C | 4/6/0.6 | transparent, amber | translucent, brown | much soap | transparent, yellow | translucent, brown | much soap |
| B/C | 4.6/0.9 | transparent, amber | translucent, brown | much soap | transparent, amber | translucent, brown | much soap |
| A/C | 6/0.3 | translucent, brown | translucent, brown | much soap | translucent, amber | translucent, brown | much soap |
| A/C | 6/0.6 | translucent, brown | translucent, brown | much soap | translucent, amber | translucent, brown | much soap |
| A/C | 6/0.9 | translucent, brown | translucent, brown | much soap | translucent, amber | translucent, brown | much soap |
| A/C | 6/1.2 | translucent, brown | translucent, brown | much soap | translucent, amber | translucent, brown | much soap |
| H/C | 4/0.3 | transparent, amber | translucent, brown | little soap | clear, yellow | transparent, amber | little soap* |
| H/C | 4/0.6 | transparent, amber | translucent, brown | little soap | transparent, yellow | transparent, amber | little soap |
| H/C | 4/0.9 | transparent, amber | translucent, brown | little soap | transparent, yellow | transparent, amber | little soap |
| H/C | 4/1.2 | transparent, amber | translucent, brown | little soap | transparent, yellow | transparent, amber | little soap |
| B/C | 4.6/0.3 | transparent, amber | translucent, brown | much soap | transparent, yellow | translucent, brown | much soap* |
| B/C | 4.6/0.6 | transparent, amber | translucent, brown | much soap | transparent, yellow | translucent, brown | much soap |
| B/C | 4.6/0.9 | translucent, brown | translucent, brown | much soap | translucent, amber | translucent, brown | much soap |

TABLE IX-continued

| Treatment | | Post Treatment Appearance Readings | | | | | |
|---|---|---|---|---|---|---|---|
| | | 30 Minutes | | | 60 Minutes | | |
| Chemical | ppm total | Top Oil | Bottom Water | I/F | Top Oil | Bottom Water | I/F |
| B/C | 4.6/ 1.2 | translucent, brown | translucent, brown | much soap | translucent, amber | translucent, brown | much soap |

*no soap on reshaking after sitting overnight.

These data demonstrate the Treatment H by itself at 4 ppm active clarified the oil the fastest. This treatment combined with treatment C at 0.3 ppm active in Stage 2 was almost as fast, produced the cleanest water and was the best treatment on reshaking after sitting overnight (a measure of complete interfacial emulsion resolution/emulsifier removal when detained at the interface of the process vessels).

To measure the effects of these extraction aids on an actual POSM wash unit, a 30 day trial was conducted. The throughput of crude styrene was varied to optimize the treatment under various conditions. The build up of soapy emulsion was monitored in both stages by examining samples taken from the mid vessel trilines. Extraction performance was measured by analyzing the second stage effluent oil for free phenol, by GC, and sodium, by AA, and by measuring the water removed from the overhead accumulator in the downstream styrene distillation unit.

Treatment H was fed at 2 to 6 ppm active to the first stage influent styrene. Treatment C was fed at 0.3 to 0.5 ppm active to either the second stage influent water or the aqueous influents to both stages.

These results are reported in Table X.

TABLE X

| Styrene Rate | Baseline | | Low Rate Test | | | | High Rate Test | | |
|---|---|---|---|---|---|---|---|---|---|
| (MPPH) | 208 | 180 | 167 | 167 | 167 | 167 | 214 | 214 | 214 |
| H to Stage 1 (ppm Act) | 0 | 0 | 4 | 4 | 6 | 2 | 2 | 4 | 6 |
| C to Stage 1 (ppm Act) | 0 | 0 | 0 | 0.3 | .03 | 0.3 | 0.3 | 0.4 | 0.5 |
| C to Stage 2 (ppm Act) | 0 | 0 | 0.3 | 0.3 | 0.3 | 0.3 | 0.3 | 0.4 | 0.5 |
| Trilines of Stable Emulsion St. 1 (#) | 3–4 avg. 3.5 | 2–4 avg. 3.0 | 2.0 | 0.5 | 1.0 | 0.5 | 1.0 | 0.5 | 0.5 |
| Trilines of Stable Emulsion St. 2 (#) | 3–4 avg. 3.5 | 2–4 avg. 3.0 | 0.5 | 0.5 | .05 | 0.5 | 1.0 | 0.5 | 0.5 |
| Frequency of I/F Dumpings (#/mo.) | 4 | 1 | 0 | 0 | 0 | 0 | 0 | 0 | 0 |
| Water Distilled Overhead (PPH) | 600–2400 avg 1300 | 200–2000 avg. 900 | 150–550, avg. 350 | | | | 500–900, avg. 700 | | |
| Na in Washed Styrene (ppm) | 2–55 avg. 10 | 5–9 avg. 7 | 2–8, avg. 5 | | | | 2–6, avg. 4 | | |
| Phenol in Washed Styrene (ppm) | 6–12 avg. 9 | 2–6 avg. 4 | 2–4 avg. 3 | 2–3 avg. 2.5 | 2 | 2–3 avg. 2.5 | 3–5 avg. 4 | 5–7 avg. 6 | 5 |

These data demonstrate that the co-addition of these two extraction aids improved the conversion of phenol to Na phenate while also improving the removal of phenates to the water or interface, and the dissolution of the phenate soaps into the water. This improved the quality of the finished styrene monomer and eliminated the withdrawal and disposal of stable emulsion.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. An improved method for extracting phenols from crude styrene with an aqueous caustic solution, the improvement comprising adding an effective amount of aromatic ammonium tailed multi-polyether headed surfactant or alkylammonium tailed multi-polyether headed surfactant or quaternary polyamine to extract phenols from said crude styrene.

2. The method as claimed in claim 1 wherein said aromatic or alkylammonium tailed multi-polyether headed surfactants are selected from the group consisting of those surfactants having hydrophobic "tails" of $C_3$ to $C_{18}$ alkylaryl diols to polyols and $C_3$ to $C_{22}$ alkyl or alkylaryl 1° or 2° amines adducted with $C_2$ to $C_3$ alkylene oxides to form two or more hydrophilic "heads" per hydrophobe having separate polyether chains of degree of polymerization 3 to 30 and the backbone and branches of the polymer contain only either or amine linkages.

3. The method as claimed in claim 2 wherein said aromatic tailed multi-polyether headed surfactants are selected from the group consisting of $C_4$ to $C_9$ alkylphenolformaldehyde condensates of degree of polymerization 4 to 8 adducted with ethylene oxide to form 4 to 8 polyether chains of degree of polymerization 4 to 7 blended with alkylammonium tailed multi-polyether headed surfactants selected from the group consisting of the halide salts of linear $C_{12}$ to $C_{22}$ alkyl 2° amines adducted with ethylene oxide to form 2 polyether chains of degree of polymerization 5 to 10.

4. The method as claimed in claim 1 wherein said quaternary polyamine has a backbone and branches containing only ether or amine linkages.

5. The method as claimed in claim 4 wherein said quaternary polyamine has a degree of polymerization of about 60 to 60,000 monomer units.

6. The method as claimed in claim 1 wherein said quaternary polyamine has an overall carbon to nitrogen or oxygen ratio of less than 10.

7. The method as claimed in claim 1 wherein said quaternary polyamine is selected from the group consisting of halides, sulfates, nitrates, phosphates, carboxylates, phenates, silicates, carbonates or hydroxides of alkyl or alkylaryl quaternary amines.

8. The method as claimed in claim 7 wherein said quaternary polyamine is selected from the group consisting of poly(diallydimethylammonium chloride), poly(N,N-dimethyl, 2-hydroxypropyleneammonium chloride), and poly(N,N-dimethyl, 3-(2-hydroxypropyleneamine) propylammonium chloride).

9. The method as claimed in claim 1 wherein said multi-polyether headed surfactant is fed to said styrene in a solvent selected from the group consisting of high boiling aromatic hydrocarbons, glycol ethers and aromatic alcohols.

10. The method as claimed in claim 1 wherein said multi-polyether headed surfactant is added to influent unwashed styrene.

11. The method as claimed in claim 1 wherein said multi-polyether headed surfactant is added to styrene that is washed but not rinsed.

12. The method as claimed in claim 1 wherein said multi-polyether headed surfactant is added in an amount ranging from 3 parts to about 30 parts per million parts of styrene.

13. The method as claimed in claim 1 wherein said quaternary polyamine is added as an aqueous solution to influent caustic wash water or both fresh rinse water and influent caustic wash water.

14. The method as claimed in claim 1 wherein said quaternary polyamine is added to water in an amount ranging from about 1 to about 100 parts of polyamine per million parts of water.

15. The method as claimed in claim 1 wherein said styrene is present in a propylene oxide styrene monomer process.

* * * * *